United States Patent
Jeppesen

(10) Patent No.: US 12,427,166 B2
(45) Date of Patent: Sep. 30, 2025

(54) ANTIFUNGAL AGENT

(71) Applicant: Aarhus Universitet, Aarhus C (DK)

(72) Inventor: Per Bendix Jeppesen, Egå (DK)

(73) Assignee: AARHUS UNIVERSITET, Aarhus C (DK)

(*) Notice: Subject to any disclaimer, the term of this patent is extended or adjusted under 35 U.S.C. 154(b) by 16 days.

(21) Appl. No.: 16/065,952

(22) PCT Filed: Dec. 23, 2016

(86) PCT No.: PCT/DK2016/050467
§ 371 (c)(1),
(2) Date: Jun. 25, 2018

(87) PCT Pub. No.: WO2017/108065
PCT Pub. Date: Jun. 29, 2017

(65) Prior Publication Data
US 2019/0008893 A1    Jan. 10, 2019

(30) Foreign Application Priority Data
Dec. 23, 2015  (DK) .......................... PA 2015 70873

(51) Int. Cl.
| | | |
|---|---|---|
| *A61K 31/785* | (2006.01) | |
| *A61K 9/00* | (2006.01) | |
| *A61K 31/14* | (2006.01) | |
| *A61K 45/06* | (2006.01) | |
| *A61P 31/10* | (2006.01) | |
| *A61M 11/00* | (2006.01) | |
| *A61M 15/00* | (2006.01) | |

(52) U.S. Cl.
CPC .......... *A61K 31/785* (2013.01); *A61K 9/0014* (2013.01); *A61K 9/0019* (2013.01); *A61K 9/0053* (2013.01); *A61K 9/0075* (2013.01); *A61K 9/0078* (2013.01); *A61K 31/14* (2013.01); *A61K 45/06* (2013.01); *A61P 31/10* (2018.01); *A61M 11/00* (2013.01); *A61M 15/009* (2013.01)

(58) Field of Classification Search
CPC ..... A61P 31/10; A61K 9/0019; A61K 9/0075; A61K 9/0014; A61K 45/06; A61K 31/14; A61K 31/785; A61K 9/0078; A61K 9/0053; A61K 2300/00; A61M 15/009; A61M 11/00
See application file for complete search history.

(56) References Cited

U.S. PATENT DOCUMENTS

| | | | | |
|---|---|---|---|---|
| 4,770,878 | A | 9/1988 | Thomas | |
| 8,709,169 | B2* | 4/2014 | Company | C11D 1/835 510/264 |
| 2003/0099717 | A1* | 5/2003 | Cabrera | A01N 37/36 424/618 |
| 2005/0089496 | A1* | 4/2005 | Lichtenberg | A01N 33/08 424/70.28 |
| 2012/0121653 | A1* | 5/2012 | Jenkins | A61P 11/02 977/773 |
| 2013/0177518 | A1* | 7/2013 | Nielsen | C11D 1/72 424/75 |
| 2016/0046892 | A1* | 2/2016 | Fast | C11D 3/3776 510/400 |

FOREIGN PATENT DOCUMENTS

| | | |
|---|---|---|
| WO | WO 2002/23990 A1 | 3/2002 |
| WO | WO 2005/097094 | 10/2005 |
| WO | WO 2011/116775 | 9/2011 |
| WO | WO 2015/044669 A1 * | 4/2015 |

OTHER PUBLICATIONS

Brandt et al.: Think Fungus—Prevention and Control of Fungal Infections, https://www.ncbi.nlm.nih.gov/pmc/articles/PMC3810766/pdf/13-1092.pdf. 2013.*
Kousha et al.: Pulmonary aspergillosis: a clinical review: https://err.ersjournals.com/content/errev/20/121/156.full.pdf. 2011.*
Srinivasan et al.: Overcoming antifungal resistance, Drug Discov Today Technol. Mar. 2014.*
Astvad et al; "First Detection of TR46/Y121F/T289A and TR34/L98H Alterations in Aspergillus fumigatus Isolates from Azole-Naive Patients in Denmark despite Negative Findings in the Environment"; Antimicrobial Agents and Chemotherapy p. 5096-5101 Sep. 2014 vol. 58 No. 9.
Sancho A, et al; "Occupational allergic contact dermatitis caused by N,N-didecyl-N-methyl-poly(oxyethyl) ammonium propionate in a dental assistant"; Contact Dermatitis, 70, 376-388, (2014).
Eucast Definitive Document E.Def 9.1, Jul. 2008: Method for the determination of broth dilution minimum inhibitory concentrations of antifungal agents for conidia forming moulds.
ECDC _ Risk assessment on the impact of environmental usage of triazoles on the development and spread of resistance to medical triazoles in *Aspergillus* species. Stockholm: ECDC; 2013).
Lass-Flörl C et al; "Epidemiology and outcome of infections due to Aspergillus terreus: 10-year single centre experience"; British Journal of Haematology, 131, 201-207; 2005.
Park, Donguk et al; "Exposure characteristics of familial cases of lung injury associated with the use of humidifier disinfectants"; Environ Health. Sep. 2, 2014;13(1):70. [Epub ahead of print].

(Continued)

*Primary Examiner* — Hong Yu
(74) *Attorney, Agent, or Firm* — DINSMORE & SHOHL LLP

(57) ABSTRACT

The present invention relates to a composition comprising a mixture of a polymeric biguanide polymer and an alkyl and/or dialkyl oxyethylene methyl ammonium salt for use as a medicament, in particular for use in treating, preventing or ameliorating a fungal disease such as aspergillosis. The present invention provides a method of treating, preventing and/or ameliorating a medical condition comprising administering the composition of the present invention to a human or animal in need thereof. A mechanical device comprising said composition is also provided.

12 Claims, No Drawings

(56) References Cited

OTHER PUBLICATIONS

Stensvold et al; "Azole-Resistant Invasive Aspergillosis: Relationship to Agriculture"; Curr Fungal Infect Rep (2012) 6:178-191; DOI 10.1007/s12281-012-0097-7.
Thornton, Christoper R.; "Breaking the mould—novel diagnostic and therapeutic strategies for invasive pulmonary aspergillosis in the immune deficient patient"; Expert Rev. Clin. Immunol. 10(6), 771-780 (2014).
Walsh, Thomas J. et al; "Treatment of Aspergillosis: Clinical Practice Guidelines of the Infectious Diseases Society of America"; IDSA Guidelines for Aspergillosis • CID 2008:46 (Feb. 1, 2008).
Larsen, Soren T. et al., Airway Effects of Inhaled Quaternary Ammonium Compounds in Mice, Basic & Clinical Pharmacology & Toxicology, 2012, 110, 537-543 Nordic Pharmacological Society Denmark.

* cited by examiner

ANTIFUNGAL AGENT

FIELD OF INVENTION

The present invention relates to a composition comprising a mixture of a polymeric biguanide polymer and an alkyl and/or dialkyl oxyethylene methyl ammonium salt for use as a medicament, in particular for use in treating, preventing or ameliorating a fungal disease such as aspergillosis. The present invention provides a method of treating, preventing and/or ameliorating a medical condition comprising administering the composition of the present invention to a human or animal in need thereof. A mechanical device comprising said composition is also provided.

BACKGROUND OF INVENTION

Aspergillosis is an infection caused by the fungus *Aspergillus* that is found indoors and outdoors. Most people breathe in *Aspergillus* spores every day without getting sick. However, people with weakened immune systems or lung diseases are at a higher risk of developing health problems due to *Aspergillus*. The majority of cases occur in people with underlying illnesses such as tuberculosis or chronic obstructive pulmonary disease (COPD), but with otherwise healthy immune systems. Acute invasive aspergillosis occurs when the immune system fails to prevent *Aspergillus* spores from entering the bloodstream via the lungs. Without an effective immune response, fungal cells are free to disseminate throughout the body and can infect major organs such as the heart and kidneys. The types of health problems caused by *Aspergillus* include allergic reactions, lung infections, and infections in other organs.

In recent years, *Aspergillus* spp. and aspergillosis have been a major focus of clinical mycology because the number of patients with this disease has risen dramatically and the disease is difficult to diagnose and treat. The number of *Aspergillus* infections has increased because more patients are at risk of being exposed to this opportunistic pathogen and it is difficult to prevent the diseases and its causes. Successful therapy depends not only on an early diagnosis, which is difficult to establish, but also on the reversal of underlying host immune defects and the timely and effective use of antifungal agents.

Current medications for treating aspergillosis include polyenes, echinocandins and triazoles. The preferred choice is triazoles including Voriconazole. Triazole therapy has become the established treatment for invasive aspergillosis and is widely used in the treatment of allergic aspergillosis and chronic pulmonary aspergillosis. Treatment of allergic aspergillosis and chronic pulmonary aspergillosis may need to continue for years or even throughout a patient's lifetime. (European Centre for Disease Prevention and Control. Risk assessment on the impact of environmental usage of triazoles on the development and spread of resistance to medical triazoles in *Aspergillus* species. Stockholm: ECDC; 2013).

However, in recent years, triazole resistance in human *Aspergillus* diseases appears to have been increasing. Triazole resistance can severely limit treatment options since alternatives, which are only available in intravenous form, have been shown to be associated with more side effects and poorer outcomes. Azole fungicides are widely used for crop protection and material preservation. They protect crops from disease, ensure yields and prevent fungal contamination of produce. It has been proposed that triazole resistance has evolved in the environment and could be driven by the selective pressure of azole fungicides. The inability to treat patients with triazoles due to multi-azole resistance would have significant impact on patient management and associated health costs. Therefore, there is a high need to develop new medicaments for use in the treatment of *Aspergillus* diseases, especially medicaments that can be used to treat diseases caused by triazole resistant *Aspergillus* fungi.

SUMMARY OF INVENTION

The inventors of the present invention have now succeeded in identifying a composition comprising the biocides polymeric biguanide polymer and alkyl and/or dialkyl oxyethylene methyl ammonium salt that represents a new and improved therapeutic tool for the treatment of Aspergillosis. These biocides are known to to act synergistically against pathogenic fungi (WO 2011/116775), but there exist no prior art, which discloses a medical use of these biocides.

In one aspect, the present invention relates to a composition comprising a mixture of:
  i. a polymeric biguanide polymer and
  ii. an alkyl and/or dialkyl oxyethylene methyl ammonium salt or pharmaceutical acceptable salts or tautomers thereof, for use as a medicament.

In a preferred embodiment, the composition of the present invention is provided for use in treating, preventing or ameliorating a fungal disease or infection. Preferably, the composition of the present invention is provided for use in treating, preventing or ameliorating aspergillosis. In particular, said aspergillosis can be invasive pulmonary aspergillosis. In a specific embodiment invasive pulmonary aspergillosis is acute invasive aspergillosis, disseminated invasive aspergillosis or chronic necrotising aspergillosis.

The aspergillosis can also be non-invasive pulmonary aspergillosis. In one embodiment said non-invasive pulmonary aspergillosis is aspergilloma and/or allergic bronchopulmonary aspergillosis.

It is preferred that said polymeric biguanide polymer is Poly-(hexamethylene-guanidium chloride). It is further preferred that said dialkyl oxyethylene methyl ammonium salt is N,N-didecyl-N-methyl-poly(oxyethyl) ammonium propionate. Thus, in a particular embodiment the composition for use according to the present invention comprises a mixture of Poly-(hexamethylene-guanidium chloride) and N,N-didecyl-N-methyl-poly(oxyethyl) ammonium propionate. In a more specific embodiment said composition for use comprises a mixture of Poly-(hexamethylene-guanidium chloride) and N,N-didecyl-N-methyl-poly(oxyethyl) ammonium propionate in a ratio of about 1:1.

The composition for use may comprise at least one further active agent. In a preferred embodiment said further active agent is suitable for treating, preventing or ameliorating aspergillosis.

In an embodiment of the present invention the composition for use is formulated for enteral, topical, oral or parenteral administration or as part of a sustained release implant. For example, the parenteral administration is intravenous, subcutaneous, intramuscular, intracranial or intraperitoneal. The topical administration can for example be dermal, epicutaneous, vaginal, intravesical, pulmonary, intranasal, intratracheal or as eye drops.

In another embodiment the composition for use is formulated for nasal, pulmonary and/or bronchial administration. In a preferred embodiment the composition for use is formulated for inhalation. In a particular preferred embodiment the composition is administered as aerosols.

The dosage requirements will vary with the particular drug composition employed, the route of administration and the particular subject being treated.

In a preferred embodiment the composition of the present invention is to be administered in a dosage of from 1 µg/kg-10,000 µg/kg body weight, such as 1 µg/kg-7,500 µg/kg, such as 1 µg/kg-5,000 µg/kg, such as 1 µg/kg-2,000 µg/kg, such as 1 µg/kg-1,000 µg/kg, such as 1 µg/kg-700 µg/kg, such as 5 µg/kg-500 µg/kg, such as 10 µg/kg to 100 µg/kg bodyweight.

In one embodiment said administration is repeated daily. In another embodiment said administration is repeated at least 1-3 times weekly, such as 2-5 times weekly, such as 3-6 times weekly. In yet another embodiment said administration is repeated 1 to 8 times daily, such as 2 to 5 times daily.

Another aspect of the present invention relates to a method of treating, preventing and/or ameliorating a medical condition comprising administering a therapeutically effective amount of a composition comprising a mixture of:
  iii. a polymeric biguanide polymer and
  iv. an alkyl and/or dialkyl oxyethylene methyl ammonium salt
or pharmaceutical acceptable salts or tautomers thereof to a human or animal in need thereof.

It is appreciated that the composition is a described herein.

Preferably said medical condition is aspergillosis. Said aspergillosis is in one embodiment invasive pulmonary aspergillosis. For example said invasive pulmonary aspergillosis is acute invasive aspergillosis, disseminated invasive aspergillosis or chronic necrotising aspergillosis.

Said aspergillosis can also be non-invasive pulmonary aspergillosis such as for example aspergilloma and/or allergic bronchopulmonary aspergillosis.

In a preferred embodiment said human or animal has an immunodeficiency.

A further aspect of the present invention relates to a composition comprising a mixture of:
  v. a polymeric biguanide polymer and
  vi. an alkyl and/or dialkyl oxyethylene methyl ammonium salt
or pharmaceutical acceptable salts or tautomers thereof and at least one additional component.

Preferably said composition is a formulation for nasal, pulmonary and/or bronchial administration. For example, the composition comprises aerosols or support formation of aerosol. In a particular embodiment said composition is a shampoo.

In a preferred embodiment said polymeric biguanide polymer is Poly-(hexamethylene-guanidium chloride) and/or wherein said dialkyl oxyethylene methyl ammonium salt is N,N-didecyl-N-methyl-poly(oxyethyl) ammonium propionate.

Another aspect of the present invention relates to a mechanical device comprising a composition comprising a mixture of:
  vii. a polymeric biguanide polymer and
  viii. an alkyl and/or dialkyl oxyethylene methyl ammonium salt
or pharmaceutical acceptable salts or tautomers thereof Preferably, said device is an inhaler or a spray bottle. In one embodiment said medical device is capable of forming aerosols. Said aerosols may in a preferred embodiment comprise aerosol particles with an average diameter of less than 1 µm.

DETAILED DESCRIPTION OF THE INVENTION

Terms and Definitions

To facilitate the understanding of the following description, a number of definitions are presented in the following paragraphs.

The term "treatment", as used anywhere herein comprises any type of therapy, which aims at terminating, preventing, ameliorating and/or reducing the susceptibility to a clinical condition as described herein. In a preferred embodiment, the term treatment relates to prophylactic treatment (i.e. a therapy to reduce the susceptibility of a clinical condition, a disorder or condition as defined herein).

Thus, "treatment," "treating," and the like, as used herein, refer to obtaining a desired pharmacologic and/or physiologic effect, covering any treatment of a pathological and/or clinical condition or disorder in a mammal, including a human. The effect may be prophylactic in terms of completely or partially preventing a disorder or symptom thereof and/or may be therapeutic in terms of a partial or complete cure for a disorder and/or adverse effect attributable to the disorder. That is, "treatment" includes (1) preventing the disorder or clinical condition from occurring or recurring in a subject, (2) inhibiting the disorder or clinical condition, such as arresting its development, (3) stopping, terminating or alleviating the disorder or clinical condition or at least symptoms associated therewith, so that the host no longer suffers from the disorder or clinical condition or its symptoms, such as causing regression of the disorder or clinical condition or its symptoms, for example, by restoring or repairing a lost, missing or defective function, or stimulating an inefficient process, or (4) relieving, alleviating, or ameliorating the disorder or clinical condition, or symptoms associated therewith, where ameliorating is used in a broad sense to refer to at least a reduction in the magnitude of a parameter, such as inflammation, pain, and/or immune deficiency.

The terms "prevent", "preventing," and "prevention", as used herein, refer to a decrease in the occurrence of symptoms or characteristics of a disorder or clinical condition. The prevention may be complete. The prevention may also be partial, such that for example the occurrence of symptoms or characteristics of a disorder in a subject is less than that which would have occurred without the present invention. Prevention also refers to reduced susceptibility to a clinical condition.

The terms "ameliorate", "ameliorating" and "amelioration", are also used separately herein to refer to a reduction of the severity of the occurrence of symptoms or characteristics of a disorder or clinical condition.

Composition for Use

It is within the scope of the present invention to provide a composition for use as a medicament, such as a composition for use in treating, ameliorating and/or preventing aspergillosis. The inventors have shown that the combined use of polymeric biguanide polymer and alkyl and/or dialkyl oxyethylene methyl ammonium salt surprisingly results in an increased and synergistic biocidal effect against aspergillosis thus minimizing the concentration required to obtain the desired therapeutic effect. Use of a 2 component biocidal composition may also reduce the risk that the microorganisms to be targeted get resistant towards the biocide composition. Further, the synergistic effect obtained when combining the two biocides reduces the amount of biocides needed to obtain a therapeutic effect thereby reducing the risk of side effects.

In one aspect, the invention relates to a composition comprising a mixture of:
ix. a polymeric biguanide polymer and
x. an alkyl and/or dialkyl oxyethylene methyl ammonium salt or pharmaceutical acceptable salts or tautomers thereof, for use as a medicament.

The composition as described herein is not limited to a specific medical use. However, certain embodiments may be directed to specific treatments or treatment regimes.

The composition may for example be used in treating, preventing or ameliorating a viral disease or infection. Examples of disease causing viruses include viruses having an icosahedral capsid. Viruses having an icosahedral capsid may for example include adenovirus, calicivirus, hepadnavirus, papovavirus, parvovirus, picornavirus and reovirus. Viruses may also include viruses having a viral envelope such as flavivirus, herpesvirus and tospovirus virus. In another embodiment the virus has a helical capsid. Viruses with a helical capsid include tobacco mosaic virus. Other viruses include bunyavirus, coronavirus, filovirus, orthomyxovirus, paramyxovirus, rhabdovirus, arenavirus, poxvirus and retrovirus.

However, in a preferred embodiment, the composition of the present invention is provided for use in treating, preventing or ameliorating a fungal disease or infection. The fungal disease or infection may for example be selected from the group consisting of cryptococcosis, coccidioidomycosis, candidiasis, Geotrichosis, Histoplasmosis, mycetomas, North American blastomycosis, phaeohyphomycosis, pythiosis, lagenidiosis, rhinosporidiosis, Sporotrichosis, mucormycosis and paracoccidioidomycosis.

In a more preferred embodiment, the composition of the present invention is for use in treating, preventing or ameliorating aspergillosis.

The term aspergillosis refers to a group of diseases which result from *Aspergillus* infection. Thus, the compositions provided herein are also suitable for use in treatment of disorders associated or resulting from *Aspergillus* infection. *Aspergillus* is a genus consisting of a few hundred fungi species. In a preferred embodiment, the *aspergillus* is a pathogenic *aspergillus*. The most common pathogenic species are *A. fumigatus* and *A. flavus* producing aflatoxin, which is a toxin and a carcinogen. The most common species causing allergic disease are *A. fumigatus* and *A. clavatus*. *Aspergillus fumigatus* is by far the most common species in human *Aspergillus* infections, constituting more than 80-90% of the isolates in most series (Lass-Florl C et al., Br J Haematol. 2005; 131(2):201-7). In one embodiment, the pathogenic *aspergillus* is selected from *A. fumigatus*, *A. flavus*, *A. lentulus* and *A. clavatus*.

Invasive pulmonary aspergillosis is a severe disease that is mainly found in severely immunocompromised patients and those with chronic obstructive pulmonary disease (COPD). Acute invasive aspergillosis or disseminated invasive aspergillosis occurs when the immune system fails to prevent *Aspergillus* spores from entering the bloodstream via the lungs. Fungal cells are then free to disseminate throughout the body and may infect major organs. Chronic necrotising aspergillosis is locally invasive and is seen primarily in patients with mild immunodeficiency or with a chronic lung disease.

Thus, in a preferred embodiment the aspergillosis is pulmonary aspergillosis or more preferably, invasive pulmonary aspergillosis. The invasive pulmonary aspergillosis may for example include acute invasive aspergillosis, disseminated invasive aspergillosis or chronic necrotising aspergillosis.

In another embodiment the aspergillosis is non-invasive pulmonary aspergillosis. Non-invasive pulmonary aspergillosis may for example include aspergilloma and allergic bronchopulmonary aspergillosis (ABPA). Aspergilloma is a fungus ball that develops in a pre-existing cavity within the lung parenchyma, while ABPA is a hypersensitivity manifestation in the lungs that almost always affects patients with asthma or cystic fibrosis. Asthma patients with very severe asthma may also be sensitised to *Aspergillus*, a condition known as severe asthma with fungal sensitization (SAFS).

In a preferred embodiment of the present invention, the polymeric biguanide polymer is Poly-(hexamethylene-guanidium chloride).

In another preferred embodiment the dialkyl oxyethylene methyl ammonium salt is N,N-didecyl-N-methyl-poly(oxyethyl) ammonium propionate.

It is preferred that the composition according to the present invention comprises a mixture of Poly-(hexamethylene-guanidium chloride) and N,N-didecyl-N-methyl-poly(oxyethyl) ammonium propionate.

In an embodiment of the invention, the one or more biocides is a mixture of poly-(hexamethylene-guanidium chloride) and N,N-didecyl-N-methyl-poly(oxyethyl) ammonium propionate in a ratio of 0.5-1.5:1-5 by weight. In another embodiment of the invention, the one or more biocides is a mixture of poly-(hexamethylene-guanidium chloride) and N,N-didecyl-N-methyl-poly(oxyethyl) ammonium propionate in a ratio of 0.8-1.2:2-4 by weight. In yet another embodiment of the invention, the one or more biocides is a mixture of poly-(hexamethylene-guanidium chloride) and N,N-didecyl-N-methyl-poly(oxyethyl) ammonium propionate in a ratio of about 1:2 by weight. In a preferred embodiment of the invention, the one or more biocides is a mixture of poly-(hexamethylene-guanidium chloride) and N,N-didecyl-N-methyl-poly(oxyethyl) ammonium propionate in a ratio of about 1:1 by weight. In yet another preferred embodiment of the invention, the one or more biocides is a mixture of poly-(hexamethylene-guanidium chloride) and N,N-didecyl-N-methyl-poly(oxyethyl) ammonium propionate in a ratio of about 1:3 by weight.

In a preferred embodiment of the present invention the one or more biocides is a mixture of Poly-(hexamethylene-guanidium chloride) (and N,N-didecyl-N-methyl-poly(oxyethyl) ammonium propionate, such as e.g. in a ratio of about 1:1, 1:1.25, 1:1.5, 1:1.75, 1:2, 1:3, 1:4, 1:5, 1.25:1, 1.5:1, 1.75:1, 2:1, 3:1, or 4:1; more preferably a mixture in a ratio of about 1:1, 1:1.25, 1:1.5, 1:1.75, 1:2, 1:3, 1.25:1, 1.5:1, 1.75:1, 2:1, or 3:1; even more preferably a mixture in a ratio of about 1:1, 1:1.25, 1:1.5, 1:1.75, 1:2, 1.25:1, 1.5:1, 1.75:1, or 2:1; yet even more preferably essentially a one to one mixture of Poly-(hexamethylene-guanidium chloride) and N,N-didecyl-N-methyl-poly(oxyethyl) ammonium propionate. This specific combination of biocides has surprisingly been found to provide a synergistically effect in reducing *aspergillus*.

In one embodiment, the composition of the present invention comprises at least one further active agent. Said further active agent can be suitable for treating, preventing or ameliorating aspergillosis. In one embodiment said agent is didecyl-dimethyl-ammonium chloride.

Pharmaceutical Formulation

Whilst it is possible for the composition of the present invention to be administered as the raw mixture of biocides, it is preferred to present them in the form of a pharmaceutical formulation. Accordingly, the present invention further provides a pharmaceutical formulation, which comprises the composition of the present invention or a pharmaceutically acceptable salt or ester thereof, as herein defined, and a pharmaceutically acceptable carrier therefor. The pharmaceutical formulations may be prepared by conventional techniques, e.g. as described in Remington: The Science and Practice of Pharmacy 2005, Lippincott, Williams & Wilkins.

The pharmaceutically acceptable carriers can be either solid or liquid. Solid form preparations include powders, tablets, pills, capsules, cachets, suppositories, and dispersible granules. A solid carrier can be one or more excipients which may also act as diluents, flavoring agents, solubilizers, lubricants, suspending agents, binders, preservatives, wetting agents, tablet disintegrating agents, or an encapsulating material.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The composition of the present invention may be formulated for parenteral administration and may be presented in unit dose form in ampoules, pre-filled syringes, small volume infusion or in multi-dose containers, optionally with an added preservative. The compositions may take such forms as suspensions, solutions, or emulsions in oily or aqueous vehicles, for example solutions in aqueous polyethylene glycol. Examples of oily or non-aqueous carriers, diluents, solvents or vehicles include propylene glycol, polyethylene glycol, vegetable oils (e.g., olive oil), and injectable organic esters (e.g., ethyl oleate), and may contain agents such as preserving, wetting, emulsifying or suspending, stabilizing and/or dispersing agents. Alternatively, the active ingredients may be in powder form, obtained by aseptic isolation of sterile solid or by lyophilisation from solution for constitution before use with a suitable vehicle, e.g., sterile, pyrogen-free water. The term "active ingredients" as used herein refers to Poly-(hexamethylene-guanidium chloride) and N,N-didecyl-N-methyl-poly(oxyethyl) ammonium propionate.

The composition of the invention may also be formulated for topical delivery. The topical formulation may include a pharmaceutically acceptable carrier adapted for topical administration. Thus, the composition may take the form of a suspension, solution, ointment, lotion, sexual lubricant, cream, foam, aerosol, spray, suppository, implant, inhalant, tablet, capsule, dry powder, syrup, balm or lozenge, for example.

Preferably, the formulation will comprise about 0.5% to 75% by weight of the active ingredient(s) with the remainder consisting of suitable pharmaceutical excipients as described herein.

Pharmaceutically acceptable salts of the instant compounds, where they can be prepared, are also intended to be covered by this invention. These salts will be ones which are acceptable in their application to a pharmaceutical use. By that it is meant that the salt will retain the biological activity of the parent compound and the salt will not have untoward or deleterious effects in its application and use in treating diseases.

Pharmaceutically acceptable salts are prepared in a standard manner. If the parent compound is a base it is treated with an excess of an organic or inorganic acid in a suitable solvent. If the parent compound is an acid, it is treated with an inorganic or organic base in a suitable solvent.

The compounds of the invention may be administered in the form of an alkali metal or earth alkali metal salt thereof, concurrently, simultaneously, or together with a pharmaceutically acceptable carrier or diluent, especially and preferably in the form of a pharmaceutical composition thereof, whether by oral, rectal, or parenteral (including subcutaneous) route, in an effective amount.

Examples of pharmaceutically acceptable acid addition salts for use in the present inventive pharmaceutical composition include those derived from mineral acids, such as for example hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, p-toluenesulphonic acids, arylsulphonic, and antifoam products such as for example Struktol®.

The composition for use as described herein can for example be formulated for enteral, topical, oral or parenteral administration or as part of a sustained release implant.

Pharmaceutical Formulations for Oral Administration

The composition of the present invention may be formulated in a wide variety of formulations for oral administration. Solid form preparations may include powders, tablets, drops, capsules, cachets, lozenges, and dispersible granules. Other forms suitable for oral administration may include liquid form preparations including emulsions, syrups, elixirs, aqueous solutions, aqueous suspensions, toothpaste, gel dentrifrice, chewing gum, or solid form preparations which are intended to be converted shortly before use to liquid form preparations, such as solutions, suspensions, and emulsions.

In powders, the carrier is a finely divided solid which is a mixture with the finely divided active component. In tablets, the active component is mixed with the carrier having the necessary binding capacity in suitable proportions and compacted in the shape and size desired. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like.

Drops according to the present invention may comprise sterile or non-sterile aqueous or oil solutions or suspensions, and may be prepared by dissolving the active ingredient in a suitable aqueous solution, optionally including a bactericidal and/or fungicidal agent and/or any other suitable preservative, and optionally including a surface active agent. Suitable solvents for the preparation of an oily solution include glycerol, diluted alcohol and propylene glycol.

Emulsions may be prepared in solutions in aqueous propylene glycol solutions or may contain emulsifying agents such as lecithin, sorbitan monooleate, or acacia. Aqueous solutions can be prepared by dissolving the active component in water and adding suitable colorants, flavors, stabilizing and thickening agents. Aqueous suspensions can be prepared by dispersing the finely divided active component in water with viscous material, such as natural or synthetic gums, resins, methylcellulose, sodium carboxymethylcellulose, and other well-known suspending agents.

In one aspect, a pharmaceutical composition deliverable from a powder inhaler, a nebulizer and/or a metered dose inhaler, is provided, wherein the composition comprises: a suspension medium comprising
  i. a polymeric biguanide polymer and
  ii. an alkyl and/or dialkyl oxyethylene methyl ammonium salt
  iii. a pharmaceutically acceptable propellant, and
  iv. respirable suspending particles,
wherein polymeric biguanide polymer (i.) and alkyl and/or dialkyl oxyethylene methyl ammonium salt (ii.) associate with the suspending particles (iv.) to form a co-suspension.

Polymeric biguanide polymer is preferably Poly-(hexamethylene-guanidium chloride) and dialkyl oxyethylene methyl ammonium salt is preferably N,N-didecyl-N-methyl-poly(oxyethyl) ammonium propionate. These active compounds are preferably present in equimolar amounts or substantially equimolar amounts.

Pharmaceutical Formulations for Parenteral Administration

The composition of the present invention may be formulated in a wide variety of formulations for parenteral administration. For example, the parenteral administration can be intravenous, subcutaneous, intramuscular, intracranial or intraperitoneal.

Injections and Infusions

For injections and infusions the formulations may take such forms as suspensions, solutions, or emulsions in oily or aqueous vehicles, for example solutions in aqueous polyethylene glycol. Alternatively, the active ingredients may be in powder form, obtained by aseptic isolation of sterile solid or by lyophilisation from solution for constitution before use with a suitable vehicle, e.g., sterile, pyrogen-free water. The formulations can be presented in unit-dose or multi-dose sealed containers, such as ampoules, vials, pre-filled syringes, infusion bags, or can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Examples of oily or non-aqueous carriers, diluents, solvents or vehicles include propylene glycol, polyethylene glycol, vegetable oils, and injectable organic esters, and may contain formulatory agents such as preserving, wetting, emulsifying or suspending, stabilizing and/or dispersing agents.

The formulations for injection will typically contain from about 0.5 to about 25% by weight of the active ingredients in solution.

Topical Delivery

The composition may also be administered topically. Regions for topical administration include the skin surface and also mucous membrane tissues of the vagina, rectum, nose, mouth, and throat. For example, the topical administration can be dermal, epicutaneous, vaginal, intravesical, pulmonary, intranasal, intratracheal or as eye drops. The composition may in particular be administered to the skin or hair. For animals, the composition may be administered to the fur. When administered to the fur or skin, the composition is preferably formulated as a shampoo or skin soap.

The topical composition will typically include a pharmaceutically acceptable carrier adapted for topical administration. Thus, the composition may take the form of a suspension, solution, ointment, lotion, sexual lubricant, cream, foam, aerosol, spray, suppository, implant, inhalant, tablet, capsule, dry powder, syrup, balm or lozenge, for example. In a preferred embodiment the composition takes the form of a shampoo. Methods for preparing such compositions are well known in the pharmaceutical industry.

The composition of the present invention may be formulated for topical administration to the epidermis as ointments, creams or lotions, or as a transdermal patch. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin or a fatty acid. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Lotions according to the present invention also include those suitable for application to the eye. An eye lotion may comprise a sterile aqueous solution optionally containing a bactericide.

Nasal, Pulmonary and Bronchial Administration

Formulations for use in nasal, pulmonary and/or bronchial administration are normally administered as aerosols in order to ensure that the aerosolized dose actually reaches the mucous membranes of the nasal passages, bronchial tract or the lung. The term "aerosol particle" is used herein to describe the liquid or solid particle suitable for nasal, bronchial or pulmonary administration, i.e., that will reach the mucous membranes.

In a preferred embodiment of the present invention the composition for use is formulated for nasal, pulmonary and/or bronchial administration. Preferably, said composition is formulated for inhalation. It is further preferred that the composition for use or the composition for use formulated for nasal, pulmonary and/or bronchial administration is administered as aerosols. Such administration is particularly useful for treatment of infections in the respiratory system, such as lung infections.

Typically aerosols are administered by use of a mechanical devices designed for pulmonary and/or bronchial delivery, including but not limited to nebulizers, metered dose inhalers, and powder inhalers. With regard to construction of the delivery device, any form of aerosolization known in the art, including but not limited to spray bottles, nebulization, atomization or pump aerosolization of a liquid formulation, and aerosolization of a dry powder formulation, can be used.

Liquid Aerosol Formulations in general contain a composition of the present invention in a pharmaceutically acceptable diluent. Pharmaceutically acceptable diluents include but are not limited to sterile water, saline, buffered saline, dextrose solution, and the like.

Formulations for dispensing from a powder inhaler device will normally comprise a finely divided dry powder containing pharmaceutical composition of the present invention (or derivative) and may also include a bulking agent, such as lactose, sorbitol, sucrose, or mannitol in amounts which facilitate dispersal of the powder from the device. Dry powder formulations for inhalation may also be formulated using powder-filled capsules, in particularly capsules the material of which is selected from among the synthetic plastics.

The formulation is formulated to the type of device employed and may involve the use of an appropriate propellant material, in addition to the usual diluents, adjuvants and/or carriers useful in therapy and known to the person skilled in the art. The propellant may be any propellant generally used in the art. Specific non-limiting examples of such useful propellants are a chlorofluorocarbon, a hydrofluorocarbon, a hydrochlorofluorocarbon, or a hydrocarbon.

The formulations of the present embodiment may also include other agents useful for pH maintenance, solution stabilization, or for the regulation of osmotic pressure.

The formulations of the present embodiment may also include other agents useful for pH maintenance, solution stabilization, or for the regulation of osmotic pressure.

Transdermal Delivery

The pharmaceutical agent-chemical modifier complexes described herein can be administered transdermally. Transdermal administration typically involves the delivery of a pharmaceutical agent for percutaneous passage of the drug into the systemic circulation of the patient. The skin sites include anatomic regions for transdermally administering the drug and include the forearm, abdomen, chest, back, buttock, mastoidal area, and the like.

Transdermal delivery is accomplished by exposing a source of the complex to a patient's skin for an extended period of time. Transdermal patches have the added advantage of providing controlled delivery of a pharmaceutical agent-chemical modifier complex to the body. Such dosage forms can be made by dissolving, dispersing, or otherwise incorporating the pharmaceutical agent-chemical modifier complex in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel. For example, a simple adhesive patch can be prepared from a backing material and an acrylate adhesive.

Vaginal Administration

The composition of the present invention may be formulated for vaginal administration. Pessaries, tampons, creams, gels, pastes, foams or sprays containing in addition to the active ingredient such carriers as are known in the art to be appropriate.

Nasal Administration

The composition of the present invention may be formulated for nasal administration. The solutions or suspensions are applied directly to the nasal cavity by conventional means, for example with a dropper, pipette or spray. The formulations may be provided in a single or multidose form. In the latter case of a dropper or pipette this may be achieved by the patient administering an appropriate, predetermined volume of the solution or suspension. In the case of a spray this may be achieved for example by means of a metering atomizing spray pump.

Enteric Coating

When desired, formulations can be prepared with enteric coatings adapted for sustained or controlled release administration of the active ingredient.

Dosages and Dosing Regimes

The dosage requirements will vary with the particular drug composition employed, the route of administration and the particular subject being treated. It will also be recognized by one of skill in the art that the optimal quantity and spacing of individual dosages of active ingredients or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound or a pharmaceutically acceptable salt thereof given per day for a defined number of days, can be ascertained using conventional It is appreciated that the composition of the present invention comprises at least 50% active ingredients, such as at least 30 wt. % active ingredients, such as at least 25 wt. % active ingredients, such as for example at least 20 wt. % active ingredients, at least 15 wt. % active ingredients, such as at least 25 wt. % active ingredients, such as for example at least 20 wt. % active ingredients, at least 15 wt. % active ingredients, such as at least 10 wt. % active ingredients, such as for example at least 8 wt. % active ingredients, at least 5 wt. % active ingredients, such as at least 4 wt. % active ingredients, such as for example at least 3 wt. % active ingredients, at least 2 wt. % active ingredients, such as at least 1 wt. % active ingredients, such as for example at least 0.5 wt. % active ingredients or at least 0.5 wt. % active ingredients.

Wt. % is an abbreviation for weight percent.

The active ingredients are polymeric biguanide polymer an alkyl and/or dialkyl oxyethylene methyl ammonium salt or pharmaceutical acceptable salts or tautomers thereof. Preferred embodiments of polymeric biguanide polymer an alkyl and/or dialkyl oxyethylene methyl ammonium salt present in the composition are as described elsewhere herein. It is preferred that the active ingredients is a mixture of poly-(hexamethylene-guanidium chloride) (e.g. Akacid Forte) and N,N-didecyl-N-methyl-poly(oxyethyl) ammonium propionate (e.g. Bardap 26). Preferred rations between the active ingredients are as described herein above.

The daily oral dosage regimen of the active ingredients or the composition according to the present invention will preferably be from about 0.01 to about 80 mg/kg of total body weight. The daily parenteral dosage regimen about 0.001 to about 80 mg/kg of total body weight. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day.

In one embodiment the composition or active ingredients is to be administered in a dosage of from 1 µg/kg-10,000 µg/kg body weight, such as 1 µg/kg-7,500 µg/kg, such as 1 µg/kg-5,000 µg/kg, such as 1 µg/kg-2,000 µg/kg, such as 1 µg/kg-1,000 µg/kg, such as 1 µg/kg-700 µg/kg, such as 5 µg/kg-500 µg/kg, such as 10 µg/kg to 100 µg/kg bodyweight.

In another embodiment the compound as described herein is to be administered in a dosage of from 1 µg/kg-1,000 µg/kg body weight, such as 1 µg/kg-500 µg/kg, such as 1 µg/kg-250 µg/kg, such as 1 µg/kg-100 µg/kg, such as 1 µg/kg-50 µg/kg, such as 1 µg/kg to 10 µg/kg bodyweight.

In yet another embodiment the compound as described herein is to be administered in a dosage of from 10 µg/kg-30,000 µg/kg body weight, such as 10 µg/kg-7,500 µg/kg, such as 10 µg/kg-5,000 µg/kg, such as 10 µg/kg-2,000 µg/kg, such as 10 µg/kg-1,000 µg/kg, such as 10 µg/kg-700 µg/kg, such as 10 µg/kg-500 µg/kg, such as 10 µg/kg to 100 µg/kg bodyweight.

The term "unit dosage form" as used herein refers to physically discrete units suitable as unitary dosages for human and animal subjects, each unit containing a predetermined quantity of a compound, alone or in combination with other agents, calculated in an amount sufficient to produce the desired effect in association with a pharmaceutically acceptable diluent, carrier, or vehicle. The specifications for the unit dosage forms of the present invention depend on the particular compound or compounds employed and the effect to be achieved, as well as the pharmacodynamics associated with each compound in the host. The dose administered should be an "effective amount" or an amount necessary to achieve an "effective level" in the individual patient.

When the "effective level" is used as the preferred endpoint for dosing, the actual dose and schedule can vary, depending on inter-individual differences in pharmacokinetics, drug distribution, and metabolism. The "effective level" can be defined, for example, as the blood or tissue level desired in the patient that corresponds to a concentration of one or more compounds according to the invention.

In one embodiment the administration of the composition as described herein is repeated at least 1, 2, 3, 4, 5 or 6 times weekly.

In one embodiment the administration of the composition according to the present invention is repeated daily. In another embodiment said administration is repeated at least 1-3 times weekly, such as 2-5 times weekly, such as 3-6 times weekly.

In a further embodiment the administration is repeated daily. The administration of the composition may for example be repeated 1, 2, 3, 4, 5, 6, 7 or 8 times daily. In one embodiment the administration is repeated 1 to 8 times daily, such as 2 to 5 times daily.

Methods

In one aspect the present invention relates to a method of treating, preventing and/or ameliorating a medical condition comprising administering a therapeutically effective amount of a composition comprising a mixture of:
  i. a polymeric biguanide polymer and
  ii. an alkyl and/or dialkyl oxyethylene methyl ammonium salt
or pharmaceutical acceptable salts or tautomers thereof to human or animal in need thereof.

The composition is as defined herein above, as either a general composition or a pharmaceutical formulation.

A method is also provided for treating a medical condition or disorder in a patient, such as aspergillosis e.g. invasive pulmonary aspergillosis, the method comprising:
i. providing a powder inhaler, a nebulizer or a metered dose inhaler comprising a pharmaceutically acceptable co-suspension, the co-suspension comprising:
  a. a polymeric biguanide polymer and
  b. an alkyl and/or dialkyl oxyethylene methyl ammonium salt
  c. a pharmaceutically acceptable propellant, and
  d. respirable suspending particles,
  wherein polymeric biguanide polymer (a.) and alkyl and/or dialkyl oxyethylene methyl ammonium salt (b.) associate with the suspending particles (d.) to form a co-suspension, and
ii. administering the co-suspension to the patient by actuating the powder inhaler, nebulizer or metered dose inhaler, wherein said administering of the co-suspension composition comprises delivering a therapeutically effective amount of biguanide polymer (a.) and alkyl and/or dialkyl oxyethylene methyl ammonium salt (b.) to the patient.

Polymeric biguanide polymer is preferably Poly-(hexamethylene-guanidium chloride) and dialkyl oxyethylene methyl ammonium salt is preferably N,N-didecyl-N-methyl-poly(oxyethyl) ammonium propionate. These active compounds are preferably present in equimolar amounts or substantially equimolar amounts.

The medical condition may for example be a viral disease or infection as described herein above.

In one embodiment the medical condition is a fungal disease or infection. The fungal disease or infection may for example be selected from cryptococcosis, coccidioidomycosis, candidiasis, Geotrichosis, Histoplasmosis, mycetomas, North American blastomycosis, phaeohyphomycosis, pythiosis, lagenidiosis, rhinosporidiosis, Sporotrichosis, mucormycosis and paracoccidioidomycosis.

In particular, the present invention relates to a method of treating, preventing and/or ameliorating aspergillosis comprising administering a therapeutically effective amount of a composition comprising a mixture of:
  i. a polymeric biguanide polymer and
  ii. an alkyl and/or dialkyl oxyethylene methyl ammonium salt
or pharmaceutical acceptable salts or tautomers thereof to human or animal in need thereof.

The aspergillosis is as described herein above. Thus, the aspergillosis is preferably invasive pulmonary aspergillosis. The invasive pulmonary aspergillosis can for example be acute invasive aspergillosis, disseminated invasive aspergillosis or chronic necrotising aspergillosis.

In another embodiment the aspergillosis is non-invasive pulmonary aspergillosis. For example, the non-invasive pulmonary aspergillosis is aspergilloma and/or allergic bronchopulmonary aspergillosis.

As discussed above, pulmonary aspergillosis or invasive pulmonary aspergillosis is a severe disease that is mainly found in immunocompromised patients. Thus, in a preferred embodiment said human or animal in need thereof has an immunodeficiency. Such immunodeficiency can be found in humans or patients following bone marrow transplants, organ transplantation or in patients with leukemia who undergo chemotherapy. Immunodeficiency also occurs in patients with AIDS and in patients with chronic granulomatous disease. Thus, in one embodiment, the human in need thereof has undergone bone marrow transplantation or organ transplantation. In another embodiment the human in need thereof is undergoing chemotherapy. In yet another embodiment the human in need thereof has AIDS and/or chronic granulomatous disease.

In another embodiment the humans or animal in need thereof has a lung diseases or a chronic lung disease. Preferably, the human in need thereof has chronic obstructive pulmonary disease (COPD). In another embodiment the human in need thereof has asthma or cystic fibrosis. Asthma patients with very severe asthma may also be sensitised to *Aspergillus*, a condition known as severe asthma with fungal sensitization (SAFS).

The animal in need thereof may for example be an animal with a fungal infection in the skin or fur. The animal in need thereof can for example have dermatofilosis. In one embodiment the animal is a mammal. The mammal may be an ungulate selected from the group consisting of domestic or wild representatives of bovidae, ovids, cervids, suids, equids and camelids. In a particular embodiment the mammal is a cow or bull, bison, buffalo, sheep, big-horn sheep, horse, pony, donkey, mule, deer, elk, caribou, goat, water buffalo, camel, llama, alpaca, cat or pig. In a preferred embodiment the animal is a horse. In particular, the horse may have a fungal infection in its hoofs such as "White Line Disease". In another preferred embodiment the animal is a dog. In particular, the animal in need thereof is a dog with dermatitis or epidermal dysplasia.

Composition

A further aspect of the present invention relates to a composition comprising a mixture of:
  i. a polymeric biguanide polymer and
  ii. an alkyl and/or dialkyl oxyethylene methyl ammonium salt or pharmaceutical acceptable salts or tautomers thereof and at least one additional component.

Preferably, said polymeric biguanide polymer is Poly-(hexamethylene-guanidium chloride) and/or wherein said dialkyl oxyethylene methyl ammonium salt is N,N-didecyl-N-methyl-poly(oxyethyl) ammonium propionate.

In a preferred embodiment said composition is a formulation for nasal, pulmonary and/or bronchial administration. Preferably, said composition is formulated for inhalation.

Formulations for use in nasal, pulmonary and/or bronchial administration are normally administered as aerosols in order to ensure that the aerosolized dose actually reaches the mucous membranes of the nasal passages, bronchial tract or the lung. The term "aerosol particle" is used herein to describe the liquid or solid particle suitable for nasal, bronchial or pulmonary administration, i.e., that will reach the mucous membranes.

Thus, it is preferred that the composition comprises aerosols or support formation of aerosol. Preferably, said aerosol comprises aerosol particles with an average diameter of less than 1 µm.

Liquid Aerosol Formulations in general contain a composition of the present invention in a pharmaceutically acceptable diluent. Pharmaceutically acceptable diluents include but are not limited to sterile water, saline, buffered saline, dextrose solution, and the like.

Formulations for dispensing from a powder inhaler device will normally comprise a finely divided dry powder containing pharmaceutical composition of the present invention (or derivative) and may also include a bulking agent, such as lactose, sorbitol, sucrose, or mannitol in amounts which facilitate dispersal of the powder from the device. Dry powder formulations for inhalation may also be formulated using powder-filled capsules, in particularly capsules the material of which is selected from among the synthetic plastics.

The formulation is formulated to the type of device employed and may involve the use of an appropriate propellant material, in addition to the usual diluents, adjuvants and/or carriers useful in therapy and known to the person skilled in the art. The propellant may be any propellant generally used in the art. Specific non-limiting examples of such useful propellants are a chlorofluorocarbon, a hydrofluorocarbon, a hydrochlorofluorocarbon, or a hydrocarbon.

As discussed above, the composition may also be used for treating fungal infections in the skin or fur. Thus, in another embodiment the composition is a shampoo.

Mechanical Device

Typically aerosols are administered by use of a mechanical devices designed for pulmonary and/or bronchial delivery, including but not limited to nebulizers, metered dose inhalers, and powder inhalers. In the context of respiratory delivery, inhalers are well known devices for administering an active agent to a subject's respiratory tract, and several different inhaler systems are currently commercially available. Dry powder inhalers, nebulizers and metered dose inhalers (MDIs) are common inhaler systems. MDIs may be used to deliver medicaments in a solubilized form or as a suspension. Typically, MDIs use a relatively high vapor pressure propellant to expel aerosolized droplets containing an active agent into the respiratory tract when the MDI is activated. Dry powder inhalers generally rely on the patient's inspiratory efforts to introduce a medicament in a dry powder form to the respiratory tract. On the other hand, nebulizers form a medicament aerosol to be inhaled by imparting energy to a liquid solution or suspension.

With regard to construction of the delivery device, any form of aerosolization known in the art, including but not limited to spray bottles, nebulization, atomization or pump aerosolization of a liquid formulation, and aerosolization of a dry powder formulation, can be used. The suspension medium should include one or more propellants. In general, suitable propellants for use as suspension mediums are those propellant gases that can be liquefied under pressure at room temperature, and upon inhalation or topical use, are safe and toxicologically innocuous. Additionally, it is desirable that the selected propellant be relatively non-reactive with the suspending particles and active agent particles.

Thus, another aspect of the present invention relates to a mechanical device comprising a composition comprising a mixture of:
  i. a polymeric biguanide polymer and
  ii. an alkyl and/or dialkyl oxyethylene methyl ammonium salt
or pharmaceutical acceptable salts or tautomers thereof The mechanical device is preferably suitable for respiratory delivery, and may be selected from dry powder inhalers, nebulizers and metered dose inhalers (MDIs) In one embodiment said mechanical device is an inhaler or a spray bottle. Thus, in one embodiment, a powder inhaler, nebulizer and/or metered dose inhaler is provided, which comprise a composition comprising a mixture of:
  i. a polymeric biguanide polymer and
  ii. an alkyl and/or dialkyl oxyethylene methyl ammonium salt
or pharmaceutical acceptable salts or tautomers thereof Preferably, said medical device is capable of forming aerosols. Preferably, said aerosol comprises aerosol particles with an average diameter of less than 1 µm. The inhaler may also comprise the composition according to the present invention formulated as a powder.

EXAMPLES

Example 1

In Vitro Susceptibility Testing of Possible New Treatment for azol Resistant *Aspergillus*

The purpose of this experiment was to investigate possible in vitro activity of a new compound with possible antifungal activity, including azol resistant *Aspergillus*. Human infection caused by azole resistant *Aspergillus fumigatus* seems to be increasing in several countries. The fact that certain types of azole resistant *Aspergillus fumigatus* (TR 34/L98H and TR46/Y121F/T289A) seems to infect patients without prior exposure to azoles is a matter of concern and underscores the importance of development of new antifungal drugs.

Materials and Method

The antifungal activity of a composition comprising Poly-(hexamethylene-guanidium chloride) and N,N-didecyl-N-methyl-poly(oxyethyl) ammonium propionate in a ratio of about 1:1 with respect to the molar amount was tested on wild type *Aspergillus fumigatus* (ATCC 204305) and azole resistant strains (TR 34/L98H and TR46/Y121F/T289A) as well as one clinical sample of *Fusarium proliferatum* and one clinical sample of *Scedosporium Apiospermum* was evaluated by means of EUCAST micro broth dilution1. This test method is currently recognized as the gold standard for in vitro susceptibility testing of filamenteus fungi. The test drug was diluted 1:30 in RPMI 1640 in order to obtain a max test concentration of 100 PPM. The test was performed three times for each test strain. The test drug was tested in the concentration range from 1-100 ppm.

The results are shown in Table 1.

TABLE 1

|  | MIC Unit | Aspergillus fumigatus ATCC 204305 | Aspergillus fumigatus TR34/ L98H | Aspergillus fumigatus TR46/Y121F/ T289A | Fusarium Proliferatum (clinical sample) | Scedosporium Apiospermum (clinical sample) |
|---|---|---|---|---|---|---|
| Itraconazol | mg/L | 0.125 | >8 | 1 | >8 | 0.25 |
| Voriconazol | mg/L | 0.5 | 4 | >16 | 4 | 0.25 |
| Amphotericin B | mg/L | 0.25 | 0.25 | 0.25 | 1 | 4 |
| Natamycin | mg/L | 4 | 4 | 2 | 4 | 2 |
| Terbinafin | mg/l | 2 | 4 | 2 | 1 | >16 |
| Test drug | PPM | <1 | <1 | <1 | <1 | <1 |
| Test drug | PPM | <1 | <1 | <1 | <1 | <1 |
| Test drug | PPM | <1 | <1 | <1 | <1 | <1 |

The results shown in Table 1 demonstrate that a composition comprising Poly-(hexamethylene-guanidium chloride) and N,N-didecyl-N-methyl-poly(oxyethyl) ammonium propionate has high antifungal activity against all tested filamenteus fungi.

REFERENCES

1. Rodriguez-Tudela J L, Arendrup M C, Arikan S, Barchiesi F, Bille J, Chryssanthou E, et al, EUCAST DEFINITIVE DOCUMENT E: DEF 9.1: Method for the determination of broth dilution minimum inhiitory concentrations of antifungal agents for conidia forming moulds. Def. 2008; 9:1-13.
2. Christen Rune Stensvold & Lise Nistrup Jorgensen & Maiken Cavling Arendrup Azole-Resistant Invasive Aspergillosis: Relationship to Agriculture Curr Fungal Infect Rep (2012) 6:178-191.
3. Astvad K M, Jensen R H, Hassan T M, Mathiasen E G, Thomsen G M, Pedersen U G, Christensen M, Hilberg O, Arendrup M C. First detection of TR46/Y121F/T289A and TR34/L98H alterations in *Aspergillus fumigatus* isolates from azole-naive patients in Denmark despite negative findings in the environment. See comment in PubMed Commons below Antimicrob Agents Chemother. 2014 September; 58(9):5096-101.

Example 2

A dog (Westy Highland) with a fungal skin infection was given the following treatment:

The formula contained: natural perfume-less detergent (shampoo approx. 60 ml) with 10 ml addition of equivalent mixed solution of hexamethylene-guanidium chloride (25% solution) and N,N-didecyl-N-methyl-poly(oxyethyl) ammonium propionate (70% solution). The formula is hereafter named biomedical shampoo (SH)

Procedure: The dog's fur was first rinsed thoroughly with warm water, after which SH was rubbed into the fur and the skin of the dog. The entirety of the dog was covered and rubbed with SH. The SH was left in the fur for between 5-10 minutes (the SH requires 5-10 minutes to work). There after the dog is rinsed and dried with a towel thoroughly. The same procedure is repeated in total 3 times with one weeks interval.

Results: The fungal skin infection was completely eliminated after the second wash, however to ensure/prevent reinfection it is strongly recommended to repeat a $3^{rd}$ wash. The dog has been free of fungus for one and half months to date without any reoccurrence.

Example 3

In vitro susceptibility testing of disinfectant with possible effect on methicillin resistant *Staphylococcus aureus* (MRSA).

The disinfectant was tested on an MRSA strain represented by international clonal lineage (CC): CC8(USA300), which is relevant in human infections. The tested disinfectant was a liquid composition comprising equimolar amounts of Poly-(hexamethylene-guanidium chloride) and N,N-didecyl-N-methyl-poly(oxyethyl) ammonium propionate. The disinfectant was diluted MH broth to a 51200 ppm suspension and thereof, two-fold dilutions were prepared ranging from 25600 to 25 pmm. CC8 (USA300) was tested by direct plating on 5% blood agar plates. After overnight growth at 35° C., only slight growth was visible on the plate containing 50 ppm disinfectant, where 3 colonies were observed, while no growth was observed on the remaining plates; cf. table 2. Thus, it is seen that the disinfectant seems to have a potent effect on *S aureus* (MRSA-CC8-USA300).

TABLE 2

Dilution series of disinfectant tested for effect on growth of MRSA-CC8-USA300 on blood agar plates.

| Concentration of disinfectant/ppm | Colony forming units |
|---|---|
| 25,600 | 0 |
| 12,800 | 0 |
| 6,400 | 0 |
| 3,200 | 0 |
| 1,600 | 0 |
| 800 | 0 |
| 400 | 0 |
| 200 | 0 |
| 100 | 0 |
| 50 | 0 |
| 25 | 3 |

The invention claimed is:

1. A method of treating and/or ameliorating fungal disease or infection comprising nasal, pulmonary and/or bronchial administration of a composition to a human or animal in need thereof, the composition comprising a therapeutically effective amount of poly-(hexamethylene guanidium chloride) and a therapeutically effective amount N,N-didecyl-N-methyl-poly(oxyethyl) ammonium propionate.

2. The method according to claim 1, wherein said infection is an infection with aspergillosis.

3. The method according to claim 2, wherein said aspergillosis is invasive pulmonary aspergillosis.

4. The method according to claim 3, wherein said invasive pulmonary aspergillosis is acute invasive aspergillosis, disseminated invasive aspergillosis or chronic necrotising aspergillosis.

5. The method according to claim 2, wherein said aspergillosis is non-invasive pulmonary aspergillosis.

6. The method according to claim 5, wherein said non-invasive pulmonary aspergillosis is aspergilloma and/or allergic bronchopulmonary aspergillosis.

7. The method according to claim 1, wherein said human or animal has an immunodeficiency.

8. The method according to claim 1, wherein the composition further comprises at least one further active agent.

9. The method according to claim 8, wherein said further active agent is suitable for treating, preventing or ameliorating aspergillosis.

10. The method according to claim 1, wherein the composition is formulated for enteral, topical, oral or parenteral administration or as part of a sustained release implant.

11. The method according to claim 1, wherein said fungal disease or infection is caused by an azole resistant fungus.

12. The method according to claim 1, wherein said composition consists of a therapeutically effective amount of poly-(hexamethylene guanidium chloride); a therapeutically effective amount N,N-didecyl-N-methyl-poly(oxyethyl) ammonium propionate; and one or more pharmaceutically acceptable excipients.

* * * * *